(12) United States Patent
Lee et al.

(10) Patent No.: US 7,897,181 B2
(45) Date of Patent: Mar. 1, 2011

(54) METHOD FOR PHOTOTHERMAL THERAPY USING POROUS SILICON AND NEAR INFRARED RADIATION

(75) Inventors: Chongmu Lee, Incheon (KR); Youngjoon Cho, Incheon (KR); Hojin Kim, Incheon (KR)

(73) Assignee: Inha-Industry Partnership Institute, Incheon (KR)

( * ) Notice: Subject to any disclaimer, the term of this patent is extended or adjusted under 35 U.S.C. 154(b) by 384 days.

(21) Appl. No.: 11/870,882

(22) Filed: Oct. 11, 2007

(65) Prior Publication Data

US 2008/0226743 A1 Sep. 18, 2008

(30) Foreign Application Priority Data

Mar. 16, 2007 (KR) ...................... 10-2007-0026090
Mar. 16, 2007 (KR) ...................... 10-2007-0026092

(51) Int. Cl.
*A61K 33/00* (2006.01)
*A61K 31/695* (2006.01)
*A61B 18/18* (2006.01)

(52) U.S. Cl. .............................. 424/600; 514/63; 606/2

(58) Field of Classification Search ........................ None
See application file for complete search history.

(56) References Cited

PUBLICATIONS

Plessis, Properties of Porous silicon nano-explosive devices, ScienceDigest, 135, 2007, 666-674, Epub Nov. 13, 2006.*
Kam et al Proc Natl Acad Sci USA Aug. 16, 2005, 102 (33).*
ChirvonyFluorescence and O generation of poroperties, Photochemistry and Photobiology, Jan. 18, 2006.*
Hirsh et al, Nanoshell-mediated near infrared thermal therapy of tumors, Proc Natl Acad Sci USA, 11 Nov. 23, 2003, V.100, No. 23, 13549.*
Chongmu Lee et al, *J. Mater. Chem.*, 2007, 17, 2648.*
Yamakoshi et al., 2003, *J. Am. Chem. Soc.*, 125:12803-12809.
Carre et al., 1987, *J. Cheim. Phys. Phys-Chim. Biol.*, 84:577-585.
Darmanyan, 1982, *Chem. Phys. Lett.* 91:396-400.
Chattopadhyay, 1984, *J. Photochem.*, 24:1-9.
Olmsted, 1980, *J. Am. Chem. Soc.*, 102:66-71.
Rossbroich, 1985, *J. Photochem.*, 31:37-48.
Heihoff et al., 1990, *Phototchem. Photobiol.*, 51:635-641.
Garner et al., 1976, "Singlet Oxygen, Reactions with Organic Compounds and Polymers", Ranby and Rabek, eds., John Wiley & Sons, New York, pp. 48-53.

* cited by examiner

*Primary Examiner*—Tracy Vivlemore
*Assistant Examiner*—Thurman Wheeler
(74) *Attorney, Agent, or Firm*—Greenlee Sullivan PC (57) ABSTRACT

The present invention relates to an agent for photodynamic therapy (PDT) containing porous silicon (PSi) and a method of quantitative measurement of reactive oxygen species (ROS) produced therefrom. Particularly, it is expected that the present invention will contribute to the development of cancer treatment without side effects by suggesting PSi, a safe and reliable new cancer drug that can destroy cancer cells through generating sufficient heat with little ROS produced if the PSi is used as nanobomb for a new PDT that kills cancer cells with heat or explosion. In addition, it is expected that the present invention will provide a reliable and reproducible method for quantitative measurement of a very small amount of ROS produced therefrom through an XRD analysis.

6 Claims, 5 Drawing Sheets

METHOD FOR PHOTOTHERMAL THERAPY USING POROUS SILICON AND NEAR INFRARED RADIATION

CROSS-REFERENCE TO RELATED APPLICATION

This application claims the benefit of Korean Patent Application No. 10-2007-0026090 and No. 10-2007-0026092, filed Mar., 16, 2007 in the Korean Intellectual Property Office, the disclosure of which is incorporated herein in its entirety by reference.

BACKGROUND OF THE INVENTION

1. Field of the Invention

The present invention relates to an agent for photodynamic therapy (PDT) containing porous silicon (PSi) and the method of quantitative measurement of reactive oxygen species (ROS) produced therefrom. Specifically, the present invention relates to an agent for PDT containing PSi that generates heat sufficient to kill cancer cells with generating little ROS and the method of quantitative measurement of a very small amount of ROS produced therefrom through X-ray diffraction (XRD) analysis.

2. Description of the Related Art

All of the current cancer treatments, such as radiation therapy, chemotherapy etc. attack rapidly proliferating cells. Unfortunately, these treatments attack not only cancer cells but also some of normal cells. As a result, the above treatments can deteriorate natural anti-tumor defense mechanism, as well as can cause fatal side effects. For example, radiation therapy or chemotherapy impairs rapidly dividing cells in the immune system and suppress anti-tumor and anti-infection response.

Besides the above side effects, the current cancer treatments do not satisfy the effect to be desired because they are lack of ability to selectively attack cancer cells. As a result, radiation therapy, chemotherapy or combination thereof cannot treat cancer effectively. Currently, the principal cancer treatment is the surgical removal of cancer cells. The surgical method is often performed together with radiation therapy and chemotherapy, and surgical amputation and treatments with high toxicity should be used in order to destroy all cancer cells in the real situation.

Photodynamic Therapy (PDT) was developed as a part of the efforts to minimize the above side effects of cancer treatments and improve total efficacy. PDT comprises administrating a photosensitizer to a human body for localization focusing on cancer cells and irradiating light having specific and appropriate wavelength to the cancer cells containing the photosensitizer. Accordingly, PDT can generate therapeutic response on specific human tissues such as cancer through a combination of a photosensitizer and site-specific irradiation because it can apply active light having appropriate wavelength to a specific site.

The traditional PDT destroys cancer cells using ROS produced during irradiation to a photosensitizer. A photosensitizer for PDT is required to satisfy following conditions;

Firstly, a high quantum yield to produce ROS, secondly, long wavelength of absorbing light, and thirdly, low toxicity in a non-irradiated state.

Therefore, aromatic molecules or dye molecules have been clinically employed as photosensitizers for the past few decades since they have potential to generate ROS. Also recently some nanomaterials, such as $TiO_2$, ZnO, Au, CNT (carbon nanotube), PSi (porous silicon), fullerenes etc. have been reported as new photosensitizers that can generate ROS.

ROS means unstable chemical species such as singlet oxygen ($^1O_2$), superoxide anion ($O_2^-$), hydroxyl radical (.OH), etc. which can cause cells irreversible damage through photobiological activities. In addition, there have been many reports on side effects arising from ROS production as follows:

First of all, the short-term side effects of light exposure include swollen skin, red flecks and pains. Also other side effects including appetite loss and a sore throat on swallowing, etc. last for more than six weeks.

Secondly, ROS causes structural and functional damage in the long term by reacting with biological molecules such as deoxyribonucleic acid (DNA), proteins and lipids.

Thirdly, this type of oxidative damage accumulated in human bodies can cause diseases such as heart disease, cancer, etc. eventually.

Recently, a new PDT technique in which single-wall carbon nanotubes (SWCNT) are used as a cancer treatment agent has been reported. The CNT used in this new PDT can absorb near infrared ray (NIR) whose wavelength range is from 700 to 800 nm and the heat released from the CNT can destroy cancer cells effectively. That is, if CNT to which folic acid or antibody is attached is administered to the cells using techniques such as endocytosis, the CNT administrated moves places where cancer cells exist in order to look for them because cancer cells contain a large number of antibody receptors. The NIR irradiation from the outside of the body at the stage allows the CNT to absorb the NIR. The CNT becomes excited through absorbing NIR energy and releases energy in the form of heat that can destroy surrounding cancer cells. The difference between the PDT based on the present invention and the traditional PDT is that the former destroys cancer cells using heat released from a photosensitizer by irradiating the NIR while the latter PDT destroys cancer cells using ROS released from a photosensitizer by irradiating visible ray. The traditional PDT can destroy only cancer cells existing near skin because visible ray can penetrate to depths of a few millimeters from human skin, but the new PDT can effectively destroy cancer cells located deep in human bodies because the NIR can penetrate human bodies well. In the new PDT, higher heat emission efficiency is preferred, while smaller amount of ROS emission causing side effects is preferred.

Anyway, it is important to know the exact ROS emission efficiency regarding photosensitizers whether it is the traditional PDT or the new PDT.

Recent work by Yamakoshi et al. shows that other unstable chemical species such as $O_2^-$ and .OH as well as $^1O_2$ are also generated by light irradiation on a photosensitizer and they also destroy cancer cells. Therefore, it is necessary to measure emission efficiency for all ROS including $^1O_2$, $O_2^-$ and .OH. Various techniques have been developed to measure the amount of ROS for the past decades, but these techniques were mostly developed to assess the quantum yield only for $^1O_2$ generation (Yoko Yamakoshi J. AM. CHEM. SOC. 125, 12803-12809 (2003); Carre, C. et al., J. Chim. Phys. Phys-Chim. Biol., 84: 577-85 (1987); Darmanyan. A. P., Chem. Physics. Lett., 91: 391-400 (1982); Chattopadhyay, S. K. et al., J. Photochem., 24: 1-9 (1984); Olmsted, J., III, J. Am. Chem. Soc. 102: 66-71 (1980); Rossbroich, G. et al., J. Photochem., 31: 37-48 (1985); Heihoff, K. et al., Photochem. Photobiol., 51:634-41 (1990); Garner, A. et al., Singlet Oxygen, Reactions with Orgnic Compounds and Polymers. B. Ranby and J. F. Rabek (eds.), John Wiley & Sons, New York, N.Y., 1976, p. 48-53.). The present invention relates to an analysis technique that can simultaneously measure the amount of ROS of every kind released from a photosensitizer upon light irradiation.

On the other hand, the following are theoretical background to measure ROS efficiently using XRD analysis:

The exact expression for the intensity of a single-phase powder specimen in an X-ray diffractometer is as follows.

$$I = \left(\frac{I_\sigma A \lambda^3}{32\pi r}\right)\left[\left(\frac{\mu_0}{4\pi}\right)^2 \frac{e^4}{m^2}\right]\left(\frac{1}{v^2}\right)\left[|F|^2 p\left(\frac{1+\cos^2 2\theta}{\sin^2\theta \cos\theta}\right)\right]\left(\frac{e^{-2M}}{2\mu}\right) \quad \text{[Expression 1]}$$

In Expression 1, I=integrated intensity per unit length of diffraction line, $I_0$=intensity of incident beam, A=cross-sectional area of incident beam, λ=wavelength of incident beam, r=radius of diffractometer circle, $\mu_0 = 4\pi \times 10^{-7}$ m kg $C^{-2}$, e=charge on electron (C), m=mass of electron (kg), v=volume of unit cell ($m^3$), F=structure factor, p=multiplicity factor, θ=Bragg angle, $e^{-2M}$=temperature factor, and μ=linear absorption coefficient ($m^{-1}$) which enters as the absorption factor ½ μ.

$$K = \left(\frac{I_\sigma A \lambda^3}{32\pi r}\right)\left[\left(\frac{\mu_0}{4\pi}\right)^2 \frac{e^4}{m^2}\right] \quad \text{[Expression 2]}$$

$$R = \left(\frac{1}{v^2}\right)\left[|F|^2 p\left(\frac{1+\cos^2 2\theta}{\sin^2\theta \cos\theta}\right)\right]e^{-2M} \quad \text{[Expression 3]}$$

$$I = \frac{KR}{2\mu} \quad \text{[Expression 4]}$$

If we put K and R as in Expression 2 and Expression 3 respectively, then the diffracted intensity is given like Expression 4. If the XRD analysis test condition is fixed in the above Expression 4, K is a constant, R depends on the kind and crystallographic orientation of the diffracted substance, and μ is the absorption coefficient of the diffracted substance.

For the ith element of a multicomponent system composed of many elements, Expression 4 can be written as below.

$$I_i = \frac{KR_i}{2\mu_m} C_i \quad \text{[Expression 5]}$$

In Expression 5, $C_i$ denotes the volume fraction of the i th element and μm the absorption coefficient of the multicomponent system. Since absorption is an atomic process, the multicomponent system can be regarded as slabs of each of pure elements as many as the number of the components, that is, a multilayer system. Similarly to Expression 4, for the ith layer of a multilayer system, Expression 3 can be expressed as below.

$$I_i = \frac{KR_i}{2\mu_T} C_i \quad \text{[Expression 6]}$$

In Expression 6, $C_i$ denotes the volume fraction of the i th layer and $\mu_T$ the absorption coefficient of the total multilayer system.

It is possible to efficiently measure the amount of ROS released from a photosensitizer during exposure to the NIR irradiation using the above expressions and the values obtained by the XRD analysis measurement.

Hence, the inventors of the present invention identified that the emission of ROS is suppressed when PSi is exposed to the NIR while studying photosensitizers with suppressed ROS generation causing many of the side effects. They also completed the present invention through developing a reliable and reproducible method to measure the amount of ROS released from PSi or CNT using XRD analysis.

SUMMARY OF THE INVENTION

The present invention provides an agent for PDT containing PSi in order to accomplish the above technological questions.

Moreover, the present invention provides the method to measure the amount of ROS produced during a photosensitizer's exposure to the NIR light using XRD analysis.

BRIEF DESCRIPTION OF THE DRAWINGS

The above and other objects, features and other advantages of the present invention will be more clearly understood from the following detailed description when taken in conjunction with the accompanying drawings, in which:

In FIG. 2 (b) the skeleton of silicon surrounding the long vertical pores contains numerous nanopores which play a very important role in generating heat although the nanopores are not clearly observable in this SEM image.

DESCRIPTION OF THE PREFERRED EMBODIMENTS

Below, a detailed description is given of the present invention.

The present invention introduces an agent for PDT containing PSi.

Concretely, the present invention provides an agent for PDT containing PSi, a photosensitizer that does not generate ROS and the agent is a therapeutic substance that can destroy cancer cells in PDT for cancer treatment.

PSi has a light emitting property with effective band gap energies ranging from 1.12 eV up to 2.5 eV due to quantum confinement effects, and includes numerous pores of various sizes and shapes.

When PSi is exposed to the NIR, it releases heat that can kill cancer cells. Here, the volumes of heat and ROS produced during the NIR irradiation depend on the porosity and pore size of the PSi, and the thickness of a PSi layer, and the structural properties of the PSi strongly depend on the production condition of the PSi.

Figure 1:
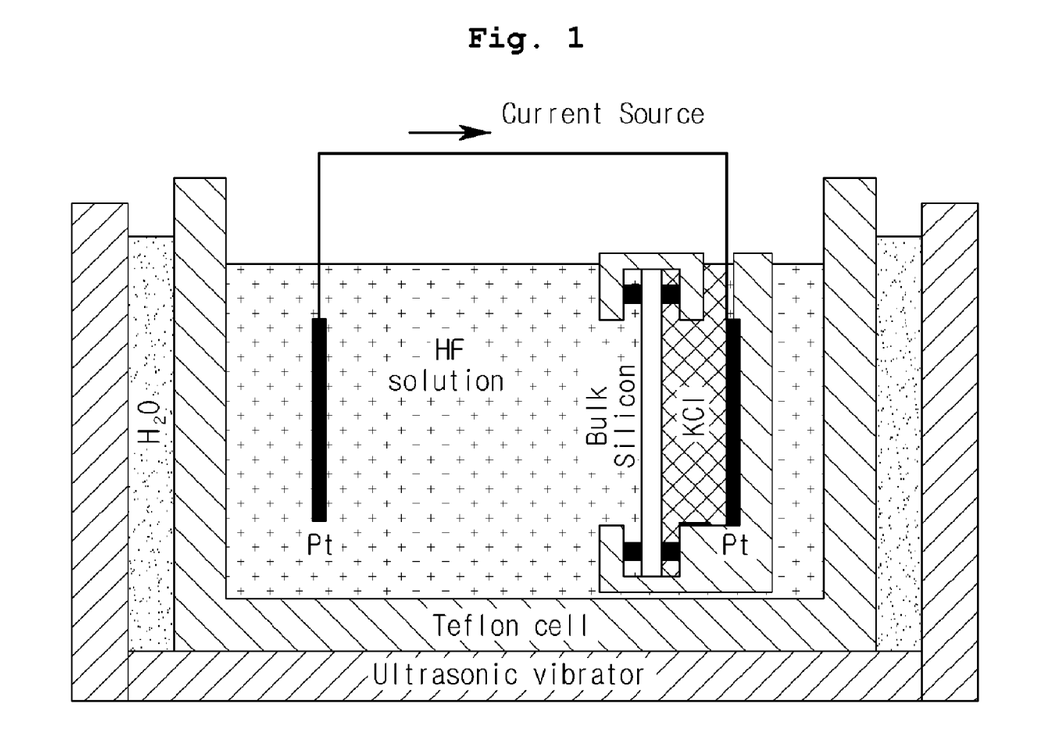
FIG. 1 is a schematic diagram showing the production method of PSi of the present invention, FIGS. 2 (a) and (b) are pictures of PSi of the present invention taken using Scanning Electron Microscopy (SEM); (a) is a top view and (b) is a side view.
Figure 2:
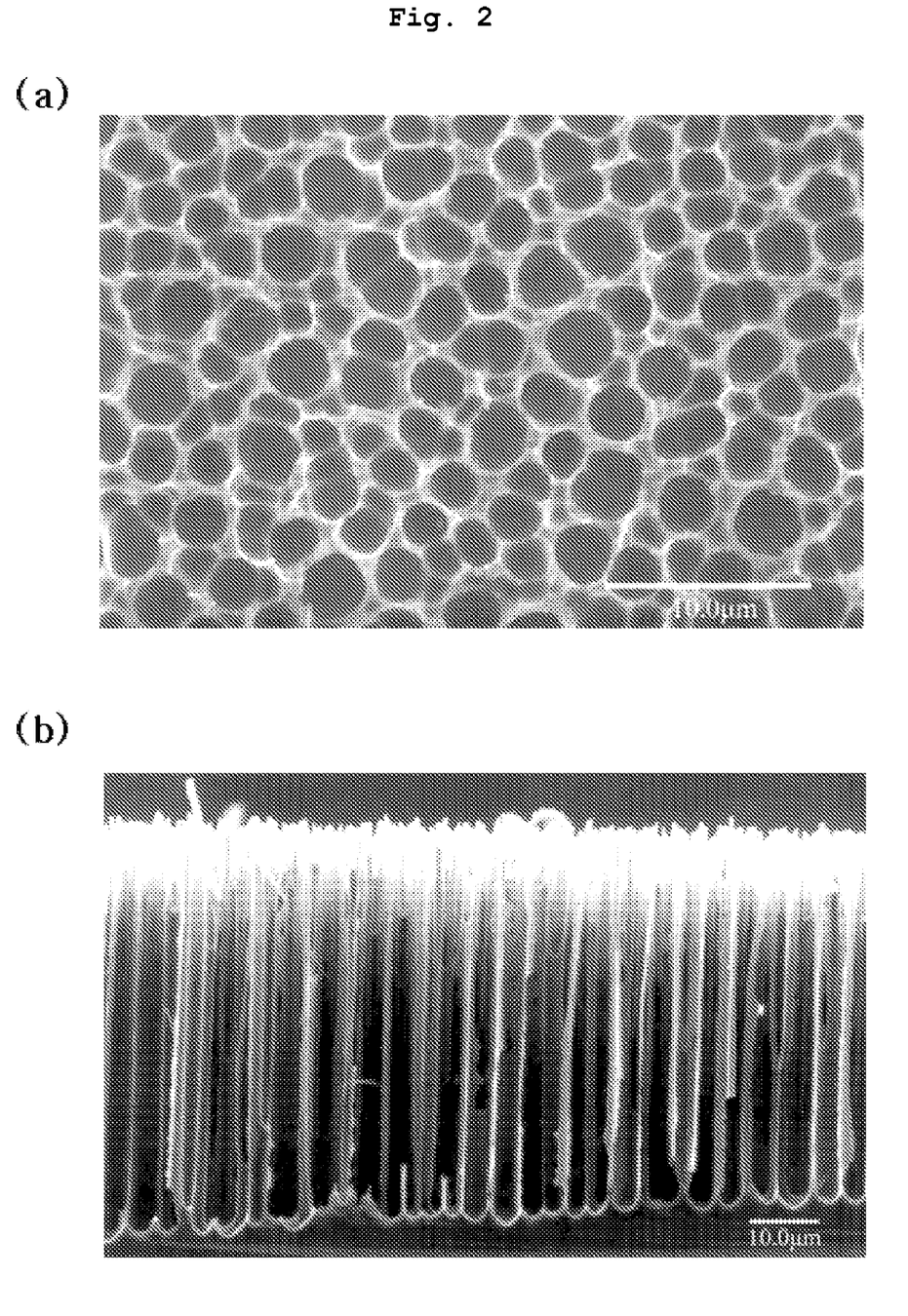

PSi can be easily formed by electrochemical etching (anodization) of bulk silicon (See FIG. 1). Anodization, a process utilizing oxidization occurring between electrolyte and the anode around the anode, connects the part to be treated to the anode while connecting a HF solution to the cathode. In this process, corrosion resistance, durability and adhesive property improve depending on the kind of the solution used after oxidization. The process is widely used as a surface treatment technique for aluminum alloy. Anodization causes rugged surfaces in most cases, which is named as porous surfaces. Generally, porous surfaces ((a) and (b) of FIG. 2) formed by anodization present high reactivity due to an increase in surface area compared with before the treatment.

Also structural properties such as the porosity and pore size of the PSi, and the thickness of a PSi layer formed by anodization strongly depend on the anodization condition. The parameters of anodization include current density, HF solution density, duration of etching, doping level of impurities in the PSi substrate, use of light during etching, etc. In general, the HF density is in inverse proportion to the porosity and the pore size. In addition, as the current density increases, the pore size and the thickness of a PSi layer show a tendency to increase accordingly. Also an increase in etching duration creates an increase in the thickness of a PSi layer, but on the other hand, the depth of the layer becomes uneven due to the chemical activity of electrolyte. In addition, ethanol can be used in order to dilute the HF solution, and the ethanol contributes to forming even pores by minimizing creation of hydrogen bubbles during anodization.

In general, the amount of heat and ROS produced during the NIR irradiation is in proportion to the porosity, pore size and the thickness of a PSi layer. However, the anodization condition should be optimized because over 70° C. is desirable for the temperature of PSi and smaller ROS generation is preferred to destroy cancer cells although a larger amount of heat generated is generally preferred.

Therefore, porosity is important for the PSi of the present invention in which 60~80% porosity to the total volume of silicon is desirable. If the porosity is 60~80%, the PSi can release heat sufficient to kill cancer cells during the NIR irradiation since it can provide large interior surface area to contact oxygen. If the porosity is less than 60%, heat emission is not sufficient to kill cancer cells. On the other hand, if the porosity is more than 80%, excessive heat emission can harm normal cells or much ROS generation can cause side effects accordingly. Also less than 10 nm pore size is desirable as illustrated in FIG. 2, but a variety of pore sizes are allowable.

PSi can be used as a drug delivery system in human bodies due to its bio-compatibility. PSi can be used as a photosensitizer or a nanobomb agent to kill cancer cells because it not only has very similar atomic and molecular structures to CNT used for the traditional PDT but also can be heated as high and quickly as CNT due to its light generation capability.

The PSi of the present invention possesses the appropriate volume of heat (it is heated up to approximately 70° C. upon exposure to the NIR irradiation for 2 minutes) and the appropriate structural property of generating much smaller ROS than CNT (approximately 0.64% of CNT) during the NIR irradiation.

Therefore, the new PDT of the present invention is a cancer treatment that can locally destroy cancer cells using heat or explosion generated from a photosensitizer during exposure to the NIR irradiation, which is different from the traditional PDT that uses ROS produced by a photosensitizer to kill cancer cells.

In the present invention, irradiating the NIR in a wavelength range from 700 to 1000 nm with a light intensity lower 3.5 W/cm$^2$ on the agent is desirable. The PSi generates heat or explosion when it is exposed to the NIR in the above range, and the heat or the explosion produced destroys cancer cells.

Also it should be noted that filtering of the NIR using a glass plate is necessary to screen the radiant heat from the NIR light source selectively when the NIR irradiation is applied to human bodies to destroy tumors inside. Otherwise, the human skin would burn because the temperature of the skin rises up as high as 60° C. after NIR irradiation at 1.5 W/cm$^2$ without the glass filter for 10 min.

In addition, the present invention includes a cancer drug containing PSi, a photosensitizer for photodynamic therapy, as an active ingredient.

The above cancer drug can treat cancer by administrating the PSi, a kind of photosensitizer that has selective adhesive property toward cancer cells, and its pharmacologically allowable salt, and performing photodynamic therapy.

At this time, the PSi is a photosensitizer for photodynamic therapy, and it can be used as a nanobomb for photodynamic therapy through being mixed with phosphate-buffered saline (PBS) solution. And the drug destroys cancer cells by releasing active heat or generating explosion during the NIR irradiation in a wavelength range from 700 to 1000 nm.

The amount of heat produced from the PSi of the present invention is nearly the same as that produced from the traditional CNT during the NIR irradiation (See FIG. 5), however there is a huge difference in the amount of ROS produced together with heat (See FIG. 1). Accordingly, the PSi of the present invention can be used a safe and reliable new cancer drug to prevent aftereffects of ROS generation because it can minimize damage caused by ROS through reducing ROS generation during the NIR irradiation on human bodies.

Further, the present invention provides the method of quantitative measurement of ROS using XRD analysis.

More specifically, the present invention provides the method of quantitative measurement of ROS using XRD analysis, comprising: preparing a photosensitizer film sample by depositing a photosensitizer on an Si substrate and coating an organic thin film on said photosensitizer, and an oxidized agent film sample by depositing an oxidized agent on a silicon substrate (Step 1); vacuum-sealing the two samples of Step 1 in one package (Step 2); preparing a photosensitizer film sample by depositing a different photosensitizer from Step 1 on a silicon substrate and the oxidized agent film sample of Step 1, and vacuum-sealing the two samples in another package (Step 3); generating ROS by irradiating the NIR in a wavelength range from 700 to 1000 nm on the two vacuum packages of Steps 2 and 3 (Step 4); and performing an XRD analyses for the oxidized oxidized agent film samples by ROS produced from the two different photosensitizer film samples respectively (Step 5).

Step 1 of the present invention preparing a photosensitizer film sample by depositing a photosensitizer on an Si substrate and coating an organic thin film on said photosensitizer, and an oxidized agent film sample by depositing an oxidized agent on a silicon substrate.

The photosensitizer releases ROS if it is exposed to light, and CNT, Au, ZnO, TiO$_2$, etc. as well as PSi of the present invention can be used as photosensitizers.

For the organic thin film, vaseline, etc. can be used as a substitute for somatic cells in case of application to human body.

Metal thin films such as Fe thin film, Cu thin film, etc. can be used to be oxidized agent, but Fe thin film is more preferable. The metal thin film is the only substance that is oxidized by ROS produced from a photosensitizer, and the film forms an oxide layer on the surface when it is exposed to ROS such as $^1O_2$, $O_2^-$ and .OH, etc. For example, a Fe thin film forms an oxidation film layer consisting of iron oxide such as FeO, Fe$_2$O$_3$, Fe$_3$O$_4$, etc. on the surface.

A photosensitizer film sample in the present invention can be obtained by depositing a photosensitizer on a 2.5 cm×2.5 cm×0.05 cm piece of p-type Si (100) and coating Vaseline on the surface of the above photosensitizer film sample deposited.

An oxidized agent film sample in the present invention can be obtained by making the thin metal film with a thickness of 1 μm using an r.f. magnetron sputtering technique and depositing the thin metal film on a 2.5 cm×2.5 cm×0.05 cm piece of p-type Si (100). At this time, native oxide films already formed on the surface of the film should be removed perfectly in order to make the thin metal film the only substance to be oxidized by ROS produced. Etching process is performed to remove the native oxide layer by dipping the sample in a diluted hydrofluoric acid (HF) solution (Deionized water: HF=50:1, v/v) for 5 minutes.

Step 2 in the present invention comprises vacuum-sealing the two samples obtained from Step 1 in a package.

Figure 3:
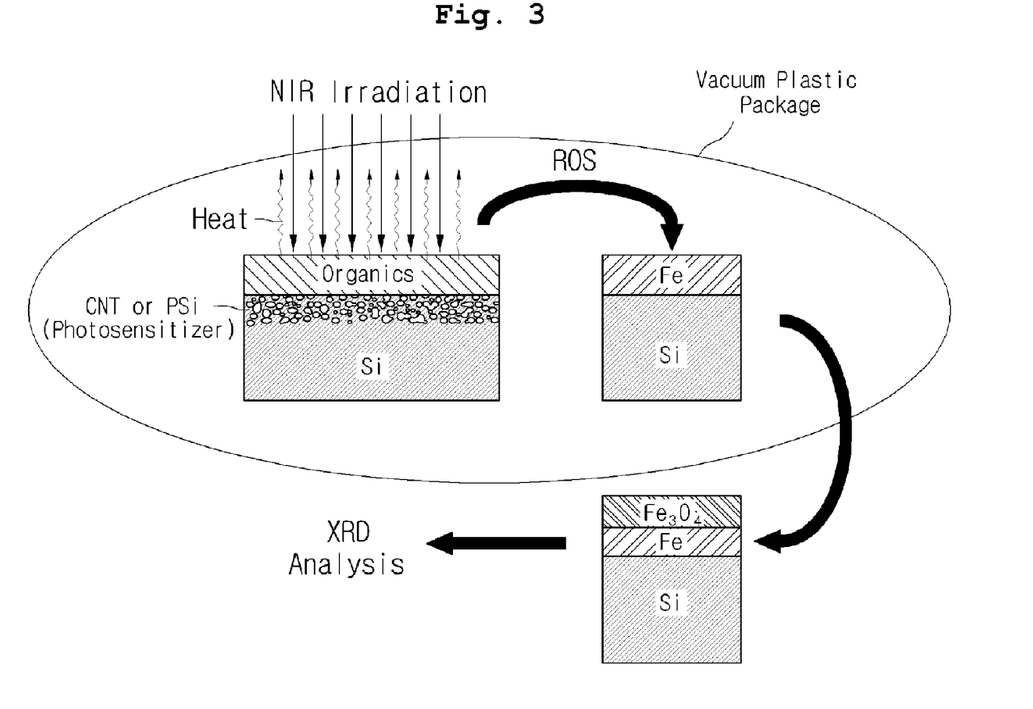
FIG. 3 is a model picture of a vacuum plastic package for measuring the amount of ROS produced by PSi or CNT during exposure to the NIR irradiation.

It is desirable to make a perfectly vacuum-sealed package by putting the photosensitizer film sample and the oxidized agent film sample of Step 1 in a plastic package together and letting the air out of the package (See FIG. 3). The vacuum package at this stage is for preventing the film from being oxidized by the air inside the package.

Step 3 in the present invention preparing a photosensitizer film sample by depositing a different photosensitizer from Step 1 on a silicon substrate and the oxidized agent film sample of Step 1, and vacuum-sealing the two samples in another package. The method of making the another package is as shown in Step 2.

Step 4 in the present invention is generating ROS by irradiating the NIR in a wavelength range from 700 to 1000 nm on the two vacuum packages of Steps 2 and 3.

At this time, the NIR in a wavelength range from 700 to 1000 nm is desirable in order to release heat sufficient to kill cancer cells from a photosensitizer. If the NIR is irradiated on the two photosensitizer film samples respectively, ROS as well as heat are produced simultaneously.

Step 5 in the present invention is performing XRD analyses for the oxidized agent film samples by ROS produced from the two different photosensitizer film samples, respectively.

In Step 4, the film is oxidized by ROS produced from a photosensitizer and then, an oxide film (for example, FeO film, $Fe_2O_3$ film, $Fe_3O_4$ film, etc. in case of Fe films) is formed on the surface.

At this time, oxidation level of the film can be identified using XRD analysis from the thickness of the oxidation film. The volume of ROS generation can be determined by the oxidation level of the oxidized film.

That is, the volume of ROS generation is determined by a difference in the XRD intensity caused from a difference in the thickness of each oxidized agent film layer with different oxidation levels by ROS produced from different photosensitizers.

The thickness ratio of each oxidized agent film layer is calculated by the below calculation process using XRD analyses.

In the case that the film is Fe, the thickness ratio of the film layer can be measured from:

$$\frac{I_{Fe_2O_3(CNT)(104)} I_{Si(PSi)(400)}}{I_{Fe_2O_3(PSi)(104)} I_{Si(CNT)(400)}} = \frac{t_{Fe_xO_y(CNT)}}{t_{Fe_xO_y(PSi)}}, \quad \text{[Expression 7]}$$

$$\frac{I_{Fe_3O_4(CNT)(440)} I_{Si(PSi)(400)}}{I_{Fe_3O_4(PSi)(440)} I_{Si(CNT)(400)}} = \frac{t_{Fe_xO_y(CNT)}}{t_{Fe_xO_y(PSi)}}, \quad \text{[Expression 8]}$$

or preferably the average value of two values.

In the above expressions, $I_{Fe_2O_3(CNT)(104)}$ denotes the diffraction intensity of Fe/Si (100) sample against $Fe_2O_3(104)$ diffraction, wherein the Fe/Si (100) sample with a formed $Fe_3O_4$ layer is taken out of a package consisting of CNT/Si (100) and Fe/Si (100) samples, $I_{Fe_2O_3(PSi)(104)}$ denotes the diffraction intensity of Fe/Si (100) sample against $Fe_2O_3(104)$ diffraction, wherein the Fe/Si (100) sample with a formed $Fe_3O_4$ layer is taken out of a package consisting of PSi/Si (100) and Fe/Si (100) samples, $I_{Fe_3O_4(CNT)(440)}$ denotes the diffraction intensity of Fe/Si (100) sample against $Fe_3O_4(440)$ diffraction, wherein the Fe/Si (100) sample with a formed $Fe_3O_4$ layer is taken out of a package consisting of CNT/Si (100) and Fe/Si (100) samples, $I_{Fe_3O_4(PSi)(440)}$ denotes the diffraction intensity of Fe/Si (100) sample against $Fe_3O_4(440)$ diffraction, wherein the Fe/Si (100) sample with a formed $Fe_3O_4$ layer is taken out of a package consisting of PSi/Si (100) and Fe/Si (100) samples, $I_{Si(PSi)(400)}$ and $I_{Si(CNT)(400)}$ denote the diffraction intensity against the silicon substrate (400) in the case of a PSi sample and the diffraction intensity against the silicon substrate (400) in the case of a CNT sample, respectively.

$t_{Fe_xO_y(CNT)}$ denotes the thickness of an oxidation film formed on the Fe film by the ROS produced from CNT, and $t_{Fe_xO_y(PSi)}$ denotes the thickness of an oxidation film formed on the Fe film by the ROS produced from PSi.

A Fe/Si (100) sample after the NIR irradiation can be expressed as $Fe_xO_y$/Fe/Si (100) because the upper part of the Fe film has been changed into $Fe_2O_3$ and $Fe_3O_4$. Since the cross-sectional areas of the $Fe_xO_y$ and Fe layers and the Si substrate in the $Fe_xO_y$/Fe/Si (100) sample are all the same, the volume fraction can be replaced by the thickness fraction. Namely, substituting $C_i$ in Expression 6 with $t_i/t_T$, Expression 9 presenting the $Fe_xO_y$ and Si (400) diffraction of the $Fe_xO_y$/Fe/Si (100) sample can be written as below.

$$I_{Fe_xO_y} = \frac{KR_{Fe_xO_y} t_{Fe_xO_y}}{2\mu_T t_T} \quad \text{[Expression 9]}$$

$$I_{Si(400)} = \frac{KR_{Si(400)} t_{Si}}{2\mu_T t_T} \quad \text{[Expression 10]}$$

In Expression 9 and Expression 10, t denotes the thickness of the sample while μ denotes absorption coefficient and a subscript denotes the entire $Fe_xO_y$/Fe/Si(100) sample.

Expression 9 divided by Expression 10 gives the below expression 11.

$$\frac{I_{Fe_xO_y}}{I_{Si(400)}} = \frac{R_{Fe_xO_y} t_{Fe_xO_y}}{R_{Si(400)} t_{Si}} \quad \text{[Expression 11]}$$

In Expression 11, if we call the Fe/Si (100) sample taken out of a package consisting of PSi/Si (100) and Fe/Si (100) samples Fe (PSi), and that taken out of a package consisting of CNT/Si(100) and Fe/Si(100) samples after the NIR irradiation Fe (CNT), respectively, and designate the $Fe_xO_y$ layer formed on the Fe (CNT) and Fe (PSi) samples by subscripts $Fe_xO_y$(CNT) and $Fe_xO_y$(PSi), respectively, we will be able to write the following expressions for each diffraction.

$$\frac{I_{Fe_xO_y(CNT)}}{I_{Si(400)}} = \frac{R_{Fe_xO_y}I_{Fe_xO_y(CNT)}}{R_{Si(400)}t_{Si}} \quad \text{[Expression 12]}$$

$$\frac{I_{Fe_xO_y(PSi)}}{I_{Si(400)}} = \frac{R_{Fe_xO_y}I_{Fe_xO_y(PSi)}}{R_{Si(400)}t_{Si}} \quad \text{[Expression 13]}$$

For the $Fe_xO_y/Fe/Si(100)$ sample, $t_{Si}$ as well as $R_{Fe_xO_y}$ and $R_{Si(400)}$ are always constant because the materials ($Fe_xO_y$ and Si), the crystallographic orientation of the $Fe_xO_y$ layer, and the thickness of the Si substrate used in the present invention are fixed. Expression 12 divided by Expression 11 gives the below Expression 14.

$$\frac{I_{Fe_xO_y(CNT)}I_{Si(PSi)(400)}}{I_{Fe_xO_y(PSi)}I_{Si(CNT)(400)}} = \frac{t_{Fe_xO_y(CNT)}}{t_{Fe_xO_y(PSi)}} \quad \text{[Expression 14]}$$

The $Fe_xO_y$ layer is composed of $Fe_2O_3$ and $Fe_3O_4$ phases and the main diffraction peaks for the $Fe_xO_y$ layer are $Fe_2O_3$ (104) and $Fe_3O_4$ (440) diffraction peaks. Here, $Fe_2O_3$(104) diffraction can be written as Expression 7 and $Fe_3O_4$(440) diffraction can be written as Expression 8 as above.

On the assumption that the ratio of the $Fe_2O_3$ phase to the $Fe_3O_4$ phase in the $Fe_xO_y$ layer is always constant, the value of $t_{Fe_xO_y(CNT)}/t_{Fe_xO_y(PSi)}$ can be obtained from Expression 7 and Expression 8.

After substituting the XRD analysis results (See Table 1) obtained from Example 1 of the present invention for the induced Expression 14, it was confirmed that the oxide film of PSi is approximately three times thinner than that of CNT and, as a result, PSi produces less ROS to oxidize Fe.

Accordingly, it is possible to conduct quantitative measurement of ROS using XRD analysis.

More detailed description of the present invention will be explained using examples and drawings as follows. However, the examples and the drawings are provided in order to help understand the present invention, therefore, it goes without saying that the features of the present invention are not restricted or limited by the examples or the drawings.

EXAMPLE 1

Measurement of the Amount of ROS Produced by PSi and CNT upon Exposure to the NIR Irradiation Step 1. Preparation of PSi/Si (100) and Fe/Si (100) Samples 1. Preparation of PSi Prior to anodization, the native oxide layer a silicon substrate was removed by dipping a bulk silicon in an acetone:methanol (3:1, v/v) mixed solution for 10 minutes, washing it adequately with deionized water and drying it with nitrogen gas. PSi was formed by electrochemical etching (anodization) in an electrolyte containing an ethanol:HF (1:1, v/v) mixed solution using the bulk silicon with the native oxide layer removed.

FIG. 1 illustrates an anodization apparatus. A reactor was produced using Teflon tolerant of HF and platinum was used for electrodes. At this time, a platinum film with a thickness of 10 nm was previously deposited at the back side of the bulk silicon using an r.f. magnetron sputtering technique. A 46% HF (ethanol:HF=1:1, v/v) solution diluted with 95% ethanol was used as electrolyte. Both sides of the bulk silicon were separated by O-ring, and then the front side of the bulk silicon was contacted with the HF solution. And current was sent to the backside of the bulk silicon using KCl, electrolyte, without a separate deposition process of the metal electrode material for ohmic contact because the bulk silicon had low specific resistance. Here, the current density was 50 $mA/cm^2$, and the etching time was 10 minutes and separate lighting was not used during etching. A PSi layer with 73% porosity and 55 μm thickness was prepared through this process. Therefore, the volume of the Si changed into PSi by anodization, namely the PSi layer, was $173 \times 10^{-4}$ $cm^3$ (1 cm×1 cm×3.14×55×$10^{-4}$ cm), and the mass of which was calculated to be 40.3 mg because the density of Si is 2,330 $kg/m^3$.

2. Preparation of PSi/Si (100) Sample

The PSi (The weight of the PSi used is 10.9 mg, or 40.3 mg×0.27 on the assumption that the density of the PSi is 27% of bulk Si.) prepared by Example 1 was deposited on a 2.5 cm×2.5 cm×0.05 cm p-type Si (100) piece. A PSi/Si (100) sample was obtained by coating an organic thin film on the surface of the Si sample with the PSi deposited using Vaseline in substitution for somatic cells.

3. Preparation of Fe/Si (100) Sample

A Fe film for detecting ROS was prepared using an r.f. magnetron sputtering technique. An 1 μm thick Fe film was deposited on a 2.5 cm×2.5 cm×0.05 cm p-type Si (100) piece. Then, a Fe/Si (100) sample for XRD analysis was obtained by dipping the Fe/Si sample in a diluted HF solution (Deionized water: HF=50:1) for 5 minutes in order to remove the native oxide layer prior to vacuum-sealing.

Step 2. Vacuum-sealing of PSi/Si (100) and Fe/Si (100) Samples

As shown in FIG. 3, a vacuum-sealed package was made by vacuum-sealing the PSi/Si (100) sample obtained from the above 2 and the Fe/Si (100) sample obtained from the above 3 together.

Step 3. Preparation of PSi/Si(100) and Fe/Si (100) Samples

1. Preparation of CNT/Si (100) Sample

CNT (11 mg, model: ASP-100F, diameter 1-1.2 nm, length 5-20 μm wire-type SWCNT) purchased from Iljin Nanotech Co., Korea, was deposited on a 2.5 cm×2.5 cm×0.05 cm p-type Si (100) piece. A CNT/Si (100) sample was obtained by coating an organic thin film on the surface of the Si sample with the CNT deposited using Vaseline in substitution for somatic cells.

2. Preparation of Fe/Si (100) Sample

A Fe film for detecting ROS was prepared using an r.f. magnetron sputtering technique. An 1 μm thick Fe film was deposited on a 2.5 cm×2.5 cm×0.05 cm p-type Si (100) piece. Then, an Fe/Si (100) sample for XRD analysis was obtained by dipping the Fe/Si sample in a diluted HF solution (Deionized water: HF=50:1) for 5 minutes in order to remove the native oxide layer prior to vacuum-sealing.

3. Vacuum-sealing of CNT/Si (100) and Fe/Si (100) Samples

As shown in FIG. 3, a vacuum-sealed package was made by vacuum-sealing the CNT/Si (100) sample obtained from the above 2 and the Fe/Si (100) sample obtained from the above 3 together.

Step 4. NIR Irradiation

The two vacuum-sealed plastic packages obtained from the steps 2 and 3 were exposed to the NIR irradiation simultaneously for 20 minutes using an NIR irradiator in an irradiation strength of 3.5 $W/cm^2$.

Step 5. XRD Analysis

XRD analysis (using a Philips X'pert diffractometer with a thin film goniometer) was performed using Cu—Kα radiation for these Fe/Si (100) samples taken out of the two packages exposed to the NIR irradiation at Step 4. XRD analysis was used to assess the degree of oxidation of the Fe film by the ROS produced during the NIR irradiation. FIG. 3 shows the measurement results. In addition, Table 1 indicates that the results of intensity ratios to the $Fe_2O_3$ (104) and $Fe_3O_4$ (440) diffraction peaks obtained from said XRD analysis. Repeated test results to ensure their reproducibility are also shown in the table.

TABLE 1

| Sample Set NO. | $\dfrac{I_{Fe_2O_3(CNT)(104)}I_{Si(PSi)(400)}}{I_{Fe_2O_3(PSi)(104)}I_{Si(CNT)(400)}}$ | $\dfrac{I_{Fe_3O_4(CNT)(440)}I_{Si(PSi)(400)}}{I_{Fe_3O_4(PSi)(440)}I_{Si(CNT)(400)}}$ |
| --- | --- | --- |
| 1 | 3.5 | 3.3 |
| 2 | 2.5 | 2.6 |
| 3 | 2.8 | 2.5 |
| Average | 2.9 ± 0.6 | 2.8 ± 0.5 |

Figure 4:
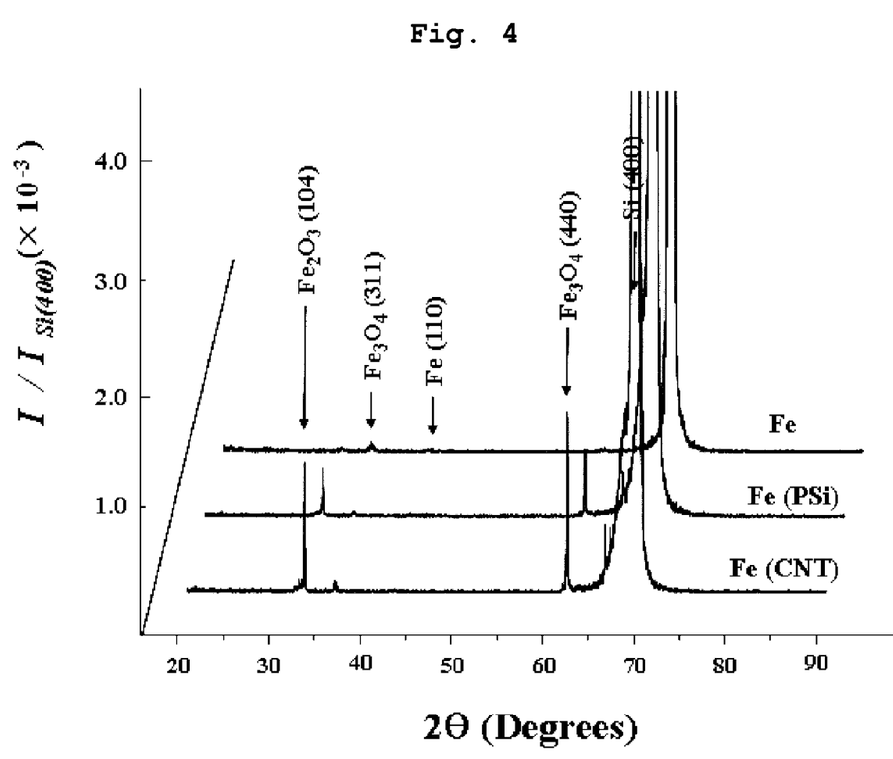
FIG. 4 is a graph showing XRD analysis results of Fe (PSi), Fe(CNT) and Fe specimens exposed to the NIR or 20 minutes.

As shown in FIG. 4, the $Fe_2O_3$ (104) and $Fe_3O_4$ (440) diffraction intensity peaks of the Fe/Si sample were much lower than those of the Fe/CNT sample.

As illustrated in Table 1, the average peak intensity ratios for the $Fe_2O_3$ (104) and $Fe_3O_4$ (440) diffraction peaks were 2.9±0.6 and 2.8±0.5, respectively. These intensity ratios can be expressed as the thicknesses of the Fe oxidation film ($Fe_2O_3$ and $Fe_3O_4$) of the sample through Expression 7 and Expression 8. They verify that PSi produces much smaller amount of ROS than CNT during the NIR irradiation. The above results imply that the thickness of the $Fe_xO_y$ layer in the Fe (PSi) sample is approximately ⅓ of that of the $Fe_xO_y$ layer in Fe (CNT) sample.

Accordingly, we may say that PSi releases approximately ⅓ of ROS of that of CNT during the NIR irradiation on the assumption that the volume of ROS is proportional to that of the $Fe_xO_y$ layer produced. If we take the fact that the amounts of the PSi and the CNT used in the experiments are 10.9 mg and 11 mg respectively into consideration, the volume of ROS produced by the same amount of PSi as CNT is only 0.64%.

EXPERIMENTAL EXAMPLE 1

Measurement of the Surface Temperatures of PSi and CNT During the NIR Irradiation The surface temperatures of PSi and CNT were measured in order to assess the amount of heat released during the NIR irradiation.

Figure 5:
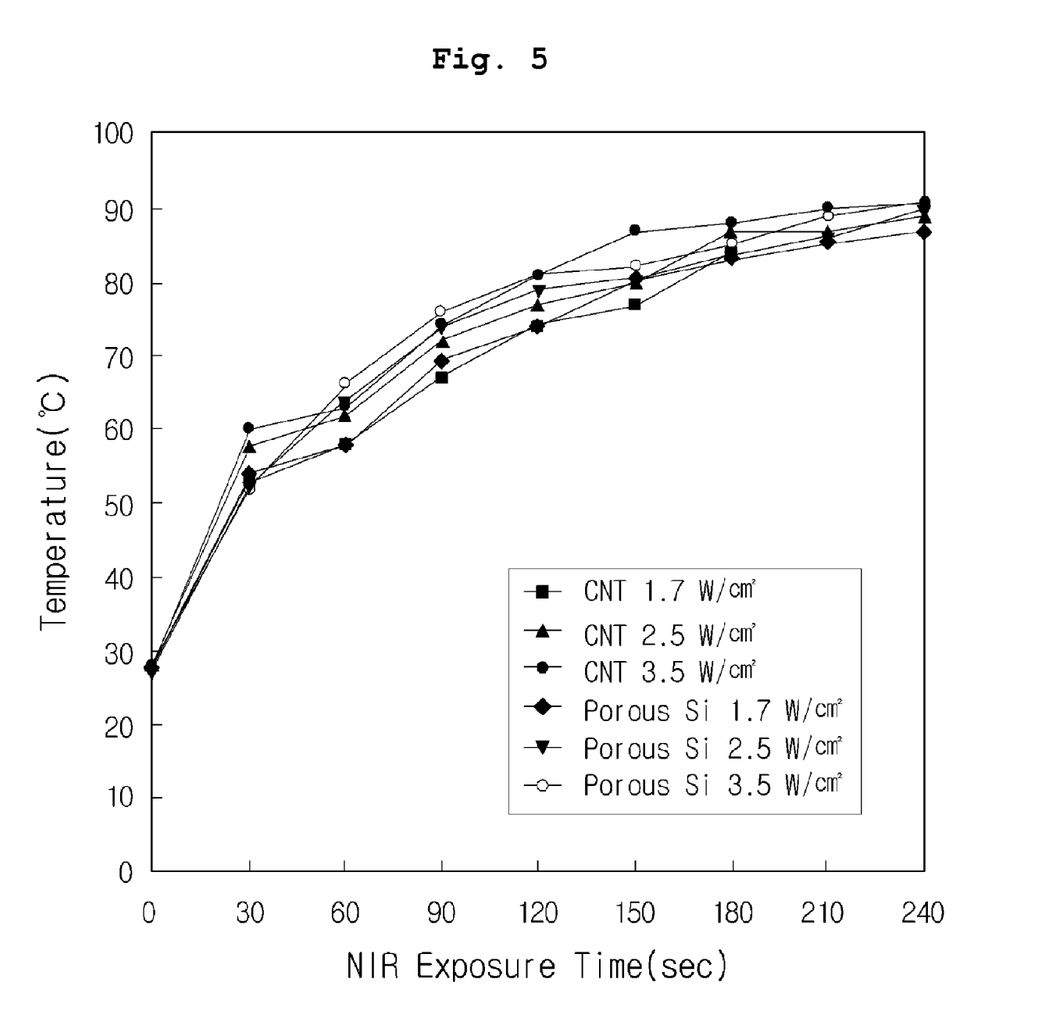
FIG. 5 is a graph showing the change of the surface temperatures of PSi and CNT exposed to the NIR for 20 minutes.

First of all, vacuum-sealed plastic packages were prepared for PSi (10.9 mg) and CNT (11 mg) respectively so as to have the same composition as examples. And the two vacuum-sealed plastic packages were exposed to the NIR irradiation for 240 seconds using an NIR irradiator in an irradiation strength of 1.7, 2.5 and 3.5 W/cm². And the surface temperatures of the two samples were measured. FIG. 5 shows the measurement results.

FIG. 5 shows change of the surface temperatures of PSi/Si (100) and CNT/Si (100) samples with the NIR exposure time for three different NIR irradiation intensities. As illustrated in FIG. 5, the change of heat generation of the PSi during the NIR irradiation was very similar to that of the CNT. As the NIR exposure time increases, the surface temperature of the PSi increased as high and quickly as that of the CNT, and the temperatures of the two nano-materials after the NIR irradiation for 240 seconds were surprisingly very similar. In the two PSi and CNT samples, the temperature increased parabolically in proportion to the NIR exposure time. The temperatures of the PSi and the CNT increased in proportion to the intensity of the NIR irradiation. And temperature differences after the NIR irradiation between 1.7 and 3.5 W/cm² were as small as 5° C. for both PSi and CNT.

INDUSTRIAL APPLICABILITY

As described hitherto, the PSi of the present invention will contribute to the development of cancer treatment without side effects by suggesting PSi, a safe and reliable new cancer drug that can destroy cancer cells through generating sufficient heat with little ROS produce. In addition, it is expected that the present invention will provide a reliable and reproducible method for quantitative measurement of a very small amount of ROS produced therefrom through XRD analysis.

What is claimed is:

1. A method of carrying out photothermal therapy to a mammal, comprising administering an agent for photothermal therapy comprising a porous silicon with 60 to 80% porosity and less than 10 nm pore size to the mammal and irradiating near infrared ray to the mammal.

2. The method according to claim 1, wherein the near infrared ray has a wavelength range from 700 to 1000 nm.

3. The method according to claim 1, wherein the agent releases active heat upon exposure to the NIR in a wavelength range from 700 to 1000 nm.

4. The method according to claim 1, wherein the photothermal therapy is used to treat cancer.

5. The method according to claim 4, wherein the near infrared ray has a wavelength range from 700 to 1000 nm.

6. The method according to claim 4, wherein the porous silicon releases heat that can kill cancer cells upon exposure to the near infrared ray.

* * * * *